(12) United States Patent
Moench et al.

(10) Patent No.: US 9,375,281 B2
(45) Date of Patent: Jun. 28, 2016

(54) LIGHT APPLICATION APPARATUS FOR APPLYING LIGHT TO AN OBJECT

(75) Inventors: Holger Moench, Vaals (NL); Bernd Ackermann, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 1105 days.

(21) Appl. No.: 13/384,803

(22) PCT Filed: Jul. 8, 2010

(86) PCT No.: PCT/IB2010/053122
§ 371 (c)(1),
(2), (4) Date: Jan. 20, 2012

(87) PCT Pub. No.: WO2011/010239
PCT Pub. Date: Jan. 27, 2011

(65) Prior Publication Data
US 2012/0116373 A1    May 10, 2012

(30) Foreign Application Priority Data

Jul. 20, 2009  (EP) .................................... 09165868

(51) Int. Cl.
*A61B 18/18*    (2006.01)
*A61B 18/20*    (2006.01)
*A61B 17/00*    (2006.01)
(Continued)

(52) U.S. Cl.
CPC ............... *A61B 18/203* (2013.01); *A61B 18/20* (2013.01); *A61B 2017/00057* (2013.01); *A61B 2018/00452* (2013.01); *A61B 2018/00476* (2013.01); *A61B 2018/00636* (2013.01); *A61B 2018/00904* (2013.01); *A61B 2018/2065* (2013.01); *A61N 2005/0629* (2013.01); *A61N 2005/0652* (2013.01)

(58) Field of Classification Search
CPC ................... A61B 18/203; A61B 2018/00476; A61B 2018/00452
USPC .......................................................... 606/9
See application file for complete search history.

(56) References Cited

U.S. PATENT DOCUMENTS 5,405,368 A    4/1995    Eckhouse
6,015,404 A    1/2000    Altshuler et al.
(Continued)

FOREIGN PATENT DOCUMENTS

DE    10120787 A1    1/2003
EP    1031324 A1    8/2000
(Continued)

*Primary Examiner* — Amanda Patton
*Assistant Examiner* — Philip Edwards

(57) ABSTRACT

The invention relates to a light application apparatus (1) for applying light to an object (3). A light source (4) generates processing light (2) and sensing light (5), which are coupled into the object (3). A light detector (8) detects the sensing light (5) after having left the object (3), and a control unit (9) controls the light source (4) such that processing light (2) in a processing time interval and sensing light (5) in a sensing time interval are alternately generated. Since processing light and sensing light are generated alternately, the generation of the processing light and of the sensing light is decoupled, i.e. the processing light can be optimized for processing purposes and the sensing light can be optimized for sensing purposes. This allows improving the quality of sensing the object and, thus, the quality of controlling the application of light depending on properties of the object.

10 Claims, 4 Drawing Sheets

(51) Int. Cl.
  *A61B 18/00* (2006.01)
  *A61N 5/06* (2006.01)

(56) References Cited

U.S. PATENT DOCUMENTS

| | | |
|---|---|---|
| 6,074,382 A | 6/2000 | Asah et al. |
| 6,190,377 B1 | 2/2001 | Kuzdrall |
| 6,533,774 B1 | 3/2003 | Ota |
| 2007/0060984 A1 | 3/2007 | Webb et al. |
| 2007/0198004 A1* | 8/2007 | Altshuler et al. .................. 606/9 |
| 2008/0154247 A1 | 6/2008 | Dallarosa et al. |
| 2009/0099499 A1* | 4/2009 | Persin et al. .................... 604/20 |

FOREIGN PATENT DOCUMENTS

| | | |
|---|---|---|
| EP | 2165669 A1 | 3/2010 |
| GB | 2372096 A | 8/2002 |
| JP | 2007252452 A | 10/2007 |
| WO | 9907438 A1 | 2/1999 |
| WO | 2000245745 A | 9/2000 |
| WO | 02085229 A2 | 10/2002 |
| WO | 2004100761 A2 | 11/2004 |
| WO | 2007106339 A2 | 9/2007 |
| WO | 2007119084 A1 | 10/2007 |

\* cited by examiner

LIGHT APPLICATION APPARATUS FOR APPLYING LIGHT TO AN OBJECT

FIELD OF THE INVENTION

The invention relates to a light application apparatus, a light application method and a computer program for applying light to an object.

BACKGROUND OF THE INVENTION

WO 2007/106339 A2 discloses a light application apparatus for applying light to the skin of a person for treating the skin, for example, for removing hair from the skin. In an embodiment, light from one or more light emitting diodes is used for treating the skin, wherein some of the light passes through the epidermis and, in particular, the dermis prior to being reflected back to a sensor. An electronic control system uses the output of the sensor to control the operation of the apparatus. This allows controlling the operation of the apparatus depending on a property of the skin.

SUMMARY OF THE INVENTION

It is an object of the present invention to provide a light application apparatus for applying light to an object, wherein the control of the application of light depending on properties of the object can be improved.

In an aspect of the present invention a light application apparatus for applying light to an object is presented, wherein the light application apparatus comprises:
 a light source for generating processing light for processing the object and sensing light for sensing the object, the light source being adapted to couple the processing light and the sensing light into the object,
 a light detector for detecting the sensing light after having left the object,
 a control unit for controlling the light source such that the light source alternately generates processing light in a processing time interval and sensing light in a sensing time interval.

Since the processing light and the sensing light are generated alternately, the generation of the processing light and of the sensing light is decoupled, i.e. the processing light can be optimized for processing purposes and the sensing light can be optimized for sensing purposes. This allows improving the quality of sensing the object and, thus, the quality of controlling the application of light depending on properties of the object.

The light source is preferentially a solid-state light source, in particular, a light emitting diode, an organic light emitted diode or a laser diode.

A solid-state light source can be switched very fast. This allows, for example, interrupting a processing of the object with the processing light only for a few milliseconds for sensing the object with the sensing light, i.e. a processing procedure can be interrupted for sensing the object, without compromising the efficiency of processing the object.

The processing light is preferentially light having a spectral emission and a power density, which allows the light to be absorbed mainly in the melanin of a hair follicle and less in the surrounding skin, in order to allow for an efficient epilation with less pain and less side effects. The processing light has preferentially a wavelength in the range of 570-1200 nm and an energy density in the range of 2-30 J/cm$^2$.

The sensing light has preferentially a wavelength within a wavelength range of 570-1200 nm and an energy density being different to the energy density of the processing light, in particular, either being smaller than the energy density of the processing light or being equal to the maximum energy density that can be produced by the light source.

The light source is adapted to couple the sensing light into the object such that the sensing light leaves the object after having traveled through the object.

The light detector is preferentially a photodiode.

The control unit can be adapted such that the light source repeatedly and alternately generates processing light in a processing time interval and sensing light in a sensing time interval. However, the control unit can also be adapted to interrupt a processing of the object only one time, in order to sense the object by using the sensing light, wherein a sensing time interval is temporally located between a first processing time interval and a second processing time interval.

A solid-state light source can be switched very fast. This allows, for example, interrupting a processing of the object with the processing light only for a few milliseconds for sensing the object with the sensing light, i.e. a processing procedure can be interrupted for sensing the object, without compromising the efficiency of processing the object.

It is preferred that the light source comprises a vertical-cavity surface-emitting laser (VCSEL). A VCSEL has a high efficiency in the above mentioned wavelength range and a spatial emission characteristic which promotes the application of the light application apparatus for removing hair on the skin of a person.

The processing of the object is preferentially a treating of the skin of a person, in particular, to remove hairs from the skin.

Preferentially the light source comprises an array of light emitting elements, in particular, an array of VCSELs, which are preferentially provided in a planar arrangement.

The light detector is preferentially arranged beside the array of light emitting elements. This arrangement of the light emitting elements and of the light detector increases the variation in distance between the light detector and the respective light emitting element. For example, if the light emitting elements are arranged in sub-groups, a light detector arranged in front of or behind the array of light emitting elements maximizes the variations of the distances between the light detector and the respective sub-group of light emitting elements. If these sub-groups emit sensing light, which is coupled into the object, which travels through the object and which is finally detected by the light detector, sensing light emitted from different sub-groups has traveled through the object with different distances. Sensing light detected by the light detector and emitted from different sub-groups is therefore differently influenced by the object, leading to an increased variety of information which can be used for controlling the light source, in particular, for controlling the generation of the processing light by the light source.

It is further preferred that the light source comprises an array of light emitting elements, wherein the spatial density of the light emitting elements is larger at an end of the array than within the array. If the array of light emitting elements is a two-dimensional array of light emitting elements, the end of the array could be regarded as the edge of the array.

Generally, a location of the object, to which the processing light is directed, is not influenced by a single light emitting element, but by several neighbored light emitting elements. Since at the end of the array of light emitting elements the light emitting elements have a reduced number of neighbors, the intensity of the processing light being used for processing the object might be reduced at the end of the array of light emitting elements, because less light emitting elements influence the respective location of the object. If at the end of the array of the light emitting elements the density of the light emitting elements is larger than within the array, this larger spatial density can counteract the reduced processing effect at the end of the array of the light emitting elements. In particular, the spatial density of the light emitting elements at the end of the array of light emitting elements is adapted such that a location of the object arranged at the end of the array of light emitting elements receives the same intensity as a location of the object arranged more centrally with respect to the array of light emitting elements.

It is further preferred that the light source comprises an array of light emitting elements in a rectangular shape having a length dimension in a length direction and a width dimension in a width direction, wherein the length dimension is larger than the width dimension.

This rectangular shape can be regarded as a one-dimensional shape. The length dimension is preferentially in the range of several centimeters and the width dimension is preferentially in the range of several millimeters. In particular, the length dimension is preferentially larger than 1 cm and preferentially smaller than 3 cm. The width dimension is preferentially larger than 1 mm and preferentially smaller than 3 mm.

It is further preferred to apply pulses of processing light with a predetermined pulse length to the skin. If a light source with a two-dimensional rectangular shape is placed upon the skin in a fixed position, then the pulse length is determined by the length of the time interval for which the light source is switched on in this position. If a light source with a one-dimensional rectangular shape is tracked across the skin in its width direction, then the pulse length is approximately equal to this width direction divided by the tracking speed.

It is further preferred that the light detector is arranged beside the array of the light emitting elements in the length direction.

This further increases the variation of distances between the light detector and the respective light emitting elements, in particular, between the light detector and the respective sub-groups, if the array of the light emitting elements is separated into sub-groups.

As already mentioned above, the array of light emitting elements is preferentially separated into sub-groups. The control unit is preferentially adapted to control the sub-groups independently from each other. For example, the control unit can be adapted to control the sub-groups independently from each other such that light emitting elements of different sub-groups emit light of different wavelengths and/or with different intensities, in order to generate a desired illumination profile. Preferentially, the light emitting elements of a same sub-group emit the same wavelength and/or emit light having the same intensity. The light detector is preferentially located at a position which has different distances to average positions of the light emitting elements of the sub-groups. Also this increases the variation of the distances of the light detector to the respective sub-groups.

It is preferred that the light source comprises an array of light emitting elements separated into sub-groups, wherein the control unit is adapted to control the light source such that only one sub-group emits sensing light at a time in the sensing time interval.

This allows easily distinguishing sensing light detected by the light detector and emitted by different sub-groups. The distance of the path, along which the respective sensing light has been traveled before being detected by the light detector, is at least approximately known. From the sensing light detected by the light detector, in particular, from the intensity of the detected sensing light, a property of the object can be determined, in particular, along the path, along which the respective sensing light has been traveled before being detected by the light detector.

It is preferred that the light application apparatus further comprises an aperture around the light detector for ensuring that light is detected which mainly comes from the object.

This aperture has preferentially the shape of a funnel.

It is further preferred that the light application apparatus comprises a velocity measurement unit for measuring the velocity of a movement of the light source with respect to the object, wherein the control unit is adapted to control the light source depending on the measured velocity. In particular, the control unit is adapted to control the light source depending on the measured velocity such that different parts of the object are illuminated similarly with the processing light, if the light source is moved with respect to the object over these parts.

This ensures that the object is processed homogenously, even if the light application apparatus is moved inhomogenously with respect to the object. The light application apparatus can preferentially be a handheld apparatus, which can be hold by a person and moved by the person with respect to the skin of the person, in order to treat different parts of the skin of the person.

It is preferred that the control unit is adapted to control the light source such that the processing light, in particular, the wavelength and/or the intensity of the processing light, is generated depending on the detected sensing light, in particular, the control unit is adapted to control the light source such that the processing light is generated depending on an amplitude of a signal generated by the light detector indicative of the detected sensing light.

The detected sensing light is indicative of a property of the object. Thus, by controlling the light source such that the processing light is generated depending on the detected sensing light, the processing of the object can be performed in accordance with a property of the object.

It is further preferred that the control unit is adapted to determine an absorption of the sensing light from the detected sensing light and to control the light source such that the processing light is generated depending on the determined absorption. This allows controlling the processing light depending on the absorption properties of the object.

The control unit can further be adapted to determine another property of the object, in particular, based on the absorption of the sensing light. For example, the skin type and/or skin tone and/or the degree of tanning can be determined based on the detected sensing light, in particular, based on the determined absorption. The control unit preferentially comprises a look-up table or a function defining an assignment between the determined property of the object, in particular, the determined absorption of the sensing light, and properties of the processing light. Thus, after the property of the object has been determined, the processing light can be generated in accordance with the properties of the processing light stored in the control unit. The corresponding assignments between the determined properties of the object and the properties of the processing light are preferentially determined by calibration measurements. For determining a property of the object depending on the detected sensing light also a look-up table or a function representing assignments between the detected sensing light and properties of the object can be used, wherein these assignments can also be determined by calibration measurements. For example, the sensing light can be applied to an object having a known property, wherein the detected sensing light is assigned to the known property of the object for generating a corresponding assignment.

It is further preferred that the light source comprises an array of light emitting elements separated into sub-groups, wherein the control unit is adapted to control the light source such that at the sensing time interval first sensing light is emitted from a first sub-group and then second sensing light is emitted from a second sub-group, wherein the first sensing light and the second sensing light are detected by the light detector, wherein the control unit is adapted to control the light source depending on the detected first sensing light and the detected second sensing light.

In particular, the control unit is preferentially adapted to control the light source such that the processing light is generated depending on the first sensing light and the second sensing light. It is further preferred that the control unit is adapted to control the light source depending on the amplitudes of a signal generated by the light detector, i.e. the control unit is adapted to control the light source depending on a first amplitude of a first signal indicative of the detected first sensing light and on a second amplitude of a second sensing signal indicative of the detected second sensing light.

These amplitudes are indicative of the optical properties of the object and thus of the penetration depth of the processing light into the object, in particular, into the skin. Thus, by adapting the control unit such that the processing light is generated depending on the detected first sensing light and the detected second sensing light, the processing light, in particular, the intensity and the wavelength, can be adapted to the respective penetration depth of the processing light into the object.

It is further preferred that the object is the skin of a human being or of an animal, wherein the control unit is adapted to determine an absorption of the first and second sensing light in the epidermis of the skin and an absorption of the first and second sensing light in the dermis of the skin from the detected first sensing light and the detected second sensing light to control the light source such that the processing light is generated depending on at least one of the determined absorption in the epidermis and the determined absorption in the dermis. In particular, the control unit is adapted to control the light source such that the processing light is generated depending on the determined absorption in the epidermis.

On its way from the light source to the light detector the sensing light passes a first time through the epidermis, then through the dermis, and finally a second time through the epidermis. The epidermis is the topmost layer of the skin and generally only about 0.1 mm thick. The epidermis contains melanin that absorbs light and determines skin tone and degree of tanning. Light scattering in the epidermis is relatively weak and can generally be neglected due to the small thickness of this layer of the skin. Underneath the epidermis is the dermis which has generally a thickness of several millimeters. In the dermis light is absorbed by hemoglobin and water. Furthermore, light is also scattered in the dermis which makes it spread parallel to the surface of the skin and reach the light detector. Light spreading from the light source to the light detector can roughly be characterized by an exponential attenuation of its intensity from the light source to the light detector according to following equation:

$$I_S = I_0 e^{-\alpha_e x_e - \alpha_d x_d}, \tag{1}$$

wherein $I_0$ is the intensity of the sensing light at the light source, $I_S$ is the intensity of the sensing light at the light detector, $\alpha_e$ represents the absorption coefficient of the epidermis, $\alpha_d$ represents the absorption coefficient of the dermis, $x_e$ is the distance traveled by the sensing light in the epidermis and $x_d$ is the distance traveled by the sensing light in the dermis. If the distance traveled by the first sensing light in the dermis is different from the distance traveled by the second sensing light in the dermis, then the first amplitude of a first signal indicative of the detected first sensing light and the second amplitude of a second signal indicative of the detected second sensing light allow for determining the absorption coefficient $\alpha_e$ of the epidermis and the absorption coefficient $\alpha_d$ of the dermis, wherein it is assumed that the distance $x_e$ traveled by the sensing light in the epidermis is twice the thickness of the epidermis which is known and about 0.1 mm and that the distance $x_d$ traveled by the sensing light in the dermis is given by the distance between the light source and the light detector. If the light source comprises an array of light emitting element arranged at different locations, the distance $x_d$ is preferentially assumed as being the distance between an average location of the light emitting elements and the location of the light detector. If the light detector comprises several light sensing elements arranged at different locations, an average location of these light sensing elements is preferentially used for determining the distance between the light source and the light detector. Then skin tone/type and degree of tanning can be determined from the absorption properties of the epidermis, i.e. from $\alpha_e$.

The absorption coefficients $\alpha_e$ and $\alpha_d$ can be regarded as effective absorption coefficients, because the absorption coefficients may not only depend on the absorption of the object, but also on scattering.

In order to control the light source such that the processing light is generated depending on the absorption of the sensing light, the control unit comprises preferentially a look-up table or a function assigning properties of the processing light to the determined absorption of the sensing light. For example, the intensity and/or the wavelength of the processing light can be assigned to absorption coefficients determined by the control unit. The assignments between the properties of the processing light and the absorption of the sensing light can be determined in advance by calibration measurements. For example, if for a skin of a human being or of an animal optimized properties of processing light are known, the absorption of the sensing light can be determined for the skin and the determined absorption can be assigned to the optimized properties of the processing light for generating an assignment, which can be stored in the control unit.

It is further preferred that the light application apparatus is an epilation apparatus.

In a further aspect of the present invention a light application method for applying light to an object is presented, wherein the light application method comprises following steps:

generating processing light for processing the object and sensing light for sensing the object by a light source and coupling the processing light and the sensing light into the object, detecting the sensing light after having left the object by a light detector, controlling the light source such that the light source alternately generates processing light in a processing time interval and sensing light in a sensing time interval by a control unit.

In a further aspect of the present invention a computer program for applying light to an object is presented, wherein the computer program comprises program code means for causing a light application apparatus for applying light to an object, the light application apparatus comprising:

a light source for generating processing light for processing the object and sensing light for sensing the object, the light source being adapted to couple the processing light and the sensing light into the object, a light detector for detecting the sensing light after having left the object, and a control unit for controlling the light source such that the light source alternately generates processing light in a processing time interval and sensing light in a sensing time interval, wherein the light source comprises an array of light emitting elements separated into sub-groups, wherein the control unit is adapted to control the light source such that at the sensing time interval first sensing light is emitted from a first sub-group and then second sensing light is emitted from a second sub-group, wherein the first sensing light and the second sensing light are detected by the light detector, wherein the control unit is adapted to control the light source depending on the detected first sensing light and the detected second sensing light; and, wherein the object is the skin of a hurman being or of an animal, wherein the control unit is further adapted to determine an absorption of the first and second sensing light in the epidermis of the skin and an absorption of the first and second sensing the detected second sensing light and to control the light source such that the processing light is generated depending on at least one of the determined absorption in the epidermis and the determined absorption in the dermis.

Furthermore the light application apparatus is configured to carry out the steps of the light application method for applying light to the skin of a human being or of an animal, the light application method comprising following steps:

generating processing light for processing the object and sensing light for sensing the object by a light source and coupling the processing light and the sensing light into the object, detecting the sensing light after having left the object by a light detector, and controlling the light source such that the light source alternately generates processing light in a processing time interval and sensing light in a sensing time interval by a control unit;

arranging the light source into an array of light emitting elements separated into subgroups, wherein the control unit is adapted to control the light source such that at the sensing time interval first sensing light is emitted from a first sub-group and then second sensing light is emitted from a second sub-group, wherein the first sensing light and the second sensing light are detected by the light detector, wherein the control unit is adapted to control the light source depending on the detected first sensing light and the detected second sensing light; and, wherein the control unit is further adapted to determine an absorption of the first and second sensing light in the epidermis of the skin and an absorption of the first and second sensing light in the dermis of the skin from the detected first sensing light andlight in the dermis of the skin from the detected first sensing light and the detected second sensing light and to control the light source such that the processing light is generated depending on at least one of the determined absorption in the epidermis and the determined absorption in the dermi when a computer program is run on a computer controlling the light application apparatus.

It shall be understood that the light application apparatus and the light application method have similar and/or identical preferred embodiments, in particular, an embodiment of the light application apparatus wherein the light source comprises a vertical-cavity surface-emitting laser, an embodiment of the light application apparatus wherein the array of light emitting elements of at least one sub-group are arranged such that the spatial density of the sub-group's light emitting elements is larger at an end of the array than within the array, an embodiment of the light application apparatus wherein the array of light emitting elements of at least one sub-group are arranged in a rectangular shape having a length dimension in a length direction and a width dimension in a width direction, wherein the length dimension is larger than the width dimension, in an alternative of this embodiment wherein the light detector is arranged beside the array of the light emitting elements in the length direction, an embodiment of the light application apparatus wherein the array of light emitting elements separated into sub groups, wherein the control unit is adapted to control the light source such that only one sub-group emits sensing light at a time in the sensing time light application apparatus wherein the control unit is adapted to determine an absorption of the sensing light from the detected sensing light and to control the light source such that the processing light is generated depending on the determined absorption, an embodiment of the light application apparatus as defined in claim 1, wherein the light application apparatus is an epilation apparatus.

It shall be understood that a preferred embodiment of the invention can also be any combination of the embodiments.

BRIEF DESCRIPTION OF THE DRAWINGS

These and other aspects of the invention will be apparent from and elucidated with reference to the embodiments described hereinafter. In the following drawings.

DETAILED DESCRIPTION OF EMBODIMENTS

Figure 1:
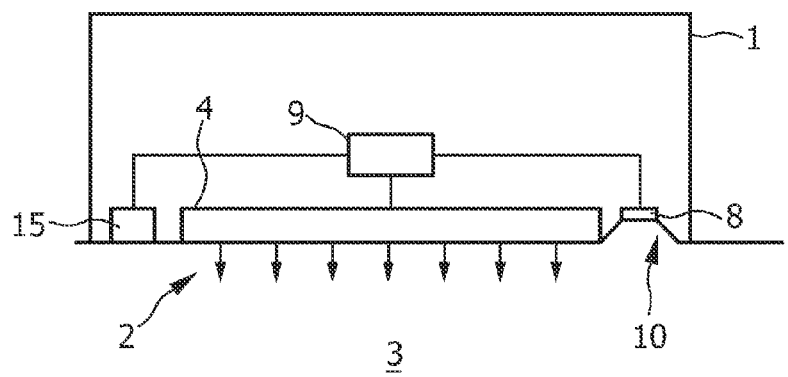
FIG. 1 shows schematically and exemplarily an embodiment of a light application apparatus during a processing time interval.

FIG. 1 shows schematically and exemplarily an embodiment of a light application apparatus for applying light to an object. The light application apparatus 1 comprises a light source 4 for generating processing light 2 for processing the object 3. In this embodiment, the object 3 is the skin of a person and the processing light is used for removing hair from the skin. The light application apparatus further comprises a control unit 9 for controlling the light source 4 such that it alternately generates processing light 2 in a processing time interval and sensing light 5 in a sensing time interval. FIG. 1 shows the light application apparatus 1 in the processing time interval, i.e. FIG. 1 shows the coupling of processing light 2 into the skin 3 for removing hair.

Figure 2:
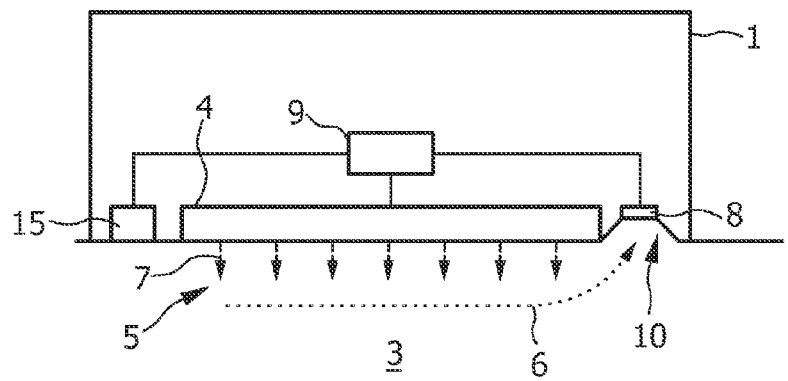
FIG. 2 shows schematically and exemplarily the light application apparatus during a sensing time interval.

FIG. 2 shows schematically and exemplarily the light application apparatus 1 in the sensing time interval. The light source 4 is adapted to generate sensing light 5 for sensing the object 3 in the sensing time interval, wherein the sensing light 5 is coupled into the object 3. This coupling of the sensing light 5 into the skin 3 is indicated by the dashed arrow 7 in FIG. 2. The sensing light travels through the object 3, which is indicated by the dotted arrow 5 in FIG. 2, and after having traveled through the object 3 the sensing light 5 leaves the object 3.

The light application 1 further comprises a light detector 8 for detecting the sensing light 5 having left the object 3.

Since processing light 2 and the sensing light 5 are generated alternately, the generation of the processing light 2 and of the sensing light 5 is decoupled. In this embodiment, the processing light 2 is optimized for processing purposes, in particular, for removing hair of the skin 3 substantially without adversely affecting the tissue of the skin, and the sensing light 5 is optimized for sensing purposes. In particular, the processing light 2 has a spectral emission and power density, which allows the processing light 2 to be absorbed mainly in the melanin of a hair follicle and less in the surrounding skin, in order to allow for an efficient hair removal with less pain and less side effects. The processing light 2 has a wavelength in the range of 570-1200 nm and an energy density in the range 2-30 J/cm$^2$. The sensing light 5 has preferentially also a wavelength in the range of 570-1200 nm, but the sensing light 5 has preferentially an intensity which differs from the intensity of the processing light 2. The control unit 9 can be adapted to control the light source 4 such that the intensity of the sensing light 5 is modified during a sensing time interval.

The light detector 8 is a photodiode in this embodiment.

The control unit 9 is adapted such that the light source 4 repeatedly and alternately generates processing light 2 in the processing time interval and sensing light 5 in the sensing time interval. The control unit 9 can also be adapted to interrupt a processing of the object 3 only one time, in order to sense the object 3 by using the sensing light 5, wherein a sensing time interval is temporally located between a first processing time interval and a second processing time interval.

In this embodiment, the light source 4 comprises an array of VCSELs in a planar arrangement. The light detector 8 is arranged beside the array of VCSELs. The array of VCSELs is schematically and exemplarily shown in FIG. 3 in more detail.

Figure 3:
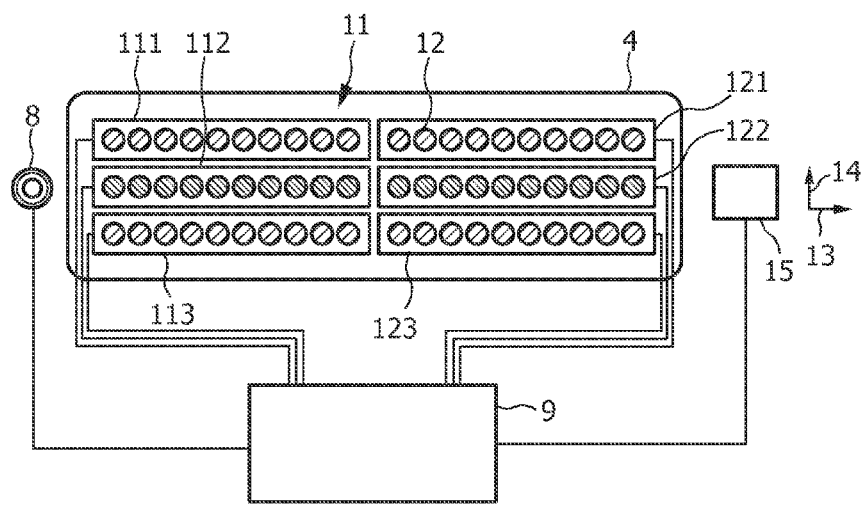
FIG. 3 shows schematically and exemplarily an array of VCSELs of the light application apparatus.

As can be seen in FIG. 3, the light source 4 comprises an array 11 of VCSELs in a rectangular shape having a length dimension in a length direction 13 and a width dimension in a width direction 14, wherein the length dimension is larger than the width dimension. This rectangular shape can be regarded as a one-dimensional shape. The length dimension is preferentially in the range of several centimeters and the width dimension is preferentially in the range of several millimeters. In this embodiment, the length dimension is larger than 1 cm and smaller than 3 cm and the width dimension is larger than 1 mm and smaller 3 mm. The light detector 8 is arranged beside the array 11 of VCSELs 12 in the length direction 13.

The array 11 of VCSELs 12 is separated into sub-groups 111, 112, 113, 121, 122, 123, wherein the control unit 9 is adapted to control the sub-groups 111, 112, 113, 121, 122, 123 independently from each other such that the VCSELs of different sub-groups 111, 112, 113, 121, 122, 123 emit light of different wavelengths and/or with different intensities, in order to generate a desired illumination profile. Preferentially, the VCSELs 12 of the same sub-group emit the same wavelength and/or emit light having the same intensity.

The light detector 8 is located at a position which has different distances to average positions of the VCSELs 12 of the respective sub-group 111, 112, 113, 121, 122, 123. The control unit 9 is preferentially adapted to control the light source 4 such that only one of the sub-groups 111, 112, 113, 121, 122, 123 emits sensing light 5 at a time in the sensing time interval. This allows easily distinguishing sensing light detected by the light detector 8 and emitted by different sub-groups.

Referring again to FIGS. 1 and 2, the light application apparatus 1 further comprises an aperture 10 around the light detector 8 for ensuring that light is detected which mainly comes from the object 3. This aperture 10 has the shape of a funnel.

The light application apparatus 1 further comprises a velocity measurement unit 15 for measuring the velocity of a movement of the light source with respect to the object, wherein the control unit 9 is adapted to control the light source 4 depending the measured velocity. In particular, the control unit 9 is adapted to control the light source 4 depending on the measured velocity such that different parts of the object 3 are illuminated similarly with the processing light 2, if the light source 4 is moved with respect to the object 3 over these parts. This ensures that the object 3 is processed homogenously, even if the light application apparatus 1 is moved inhomogenously with respect to the object 3.

The velocity measurement unit 15 preferentially comprises an optical mouse sensor and a timer. The optical mouse sensor measures displacement of the light source and the timer measures time. Therefrom the velocity of the light source is calculated as displacement divided by time. Optical mouse sensors illuminate a surface with light emitted from a light-emitting diode or laser diode and detect the light reflected from the surface. Optical mouse sensors are, for example, available from Avago, Philips, and ST Microelectronics.

Figure 4:
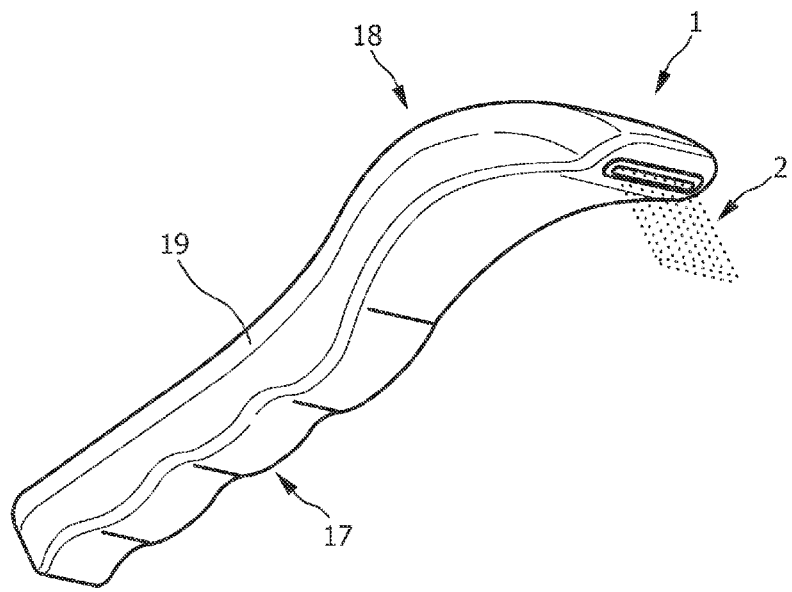
FIG. 4 shows schematically and exemplarily an outer casing of the light application apparatus being formed as an handheld apparatus.

The light application apparatus 1 is preferentially formed as a handheld apparatus, which is schematically and exemplarily shown in FIG. 4. The elements described above with reference to FIGS. 1 to 3 are preferentially located within a casing 19 comprising a handheld portion 17, which is preferentially used for holding the light application 1 in a hand, and a light emitting portion 18, which comprises at least the light source 4 for emitting processing light 2 and sensing light 5 alternately. This application apparatus 1, which is formed as a handheld apparatus, can be hold by a person and moved by the person with respect to the skin 3 of the person, in order to treat different parts of the skin 3 of the person.

Figure 5:
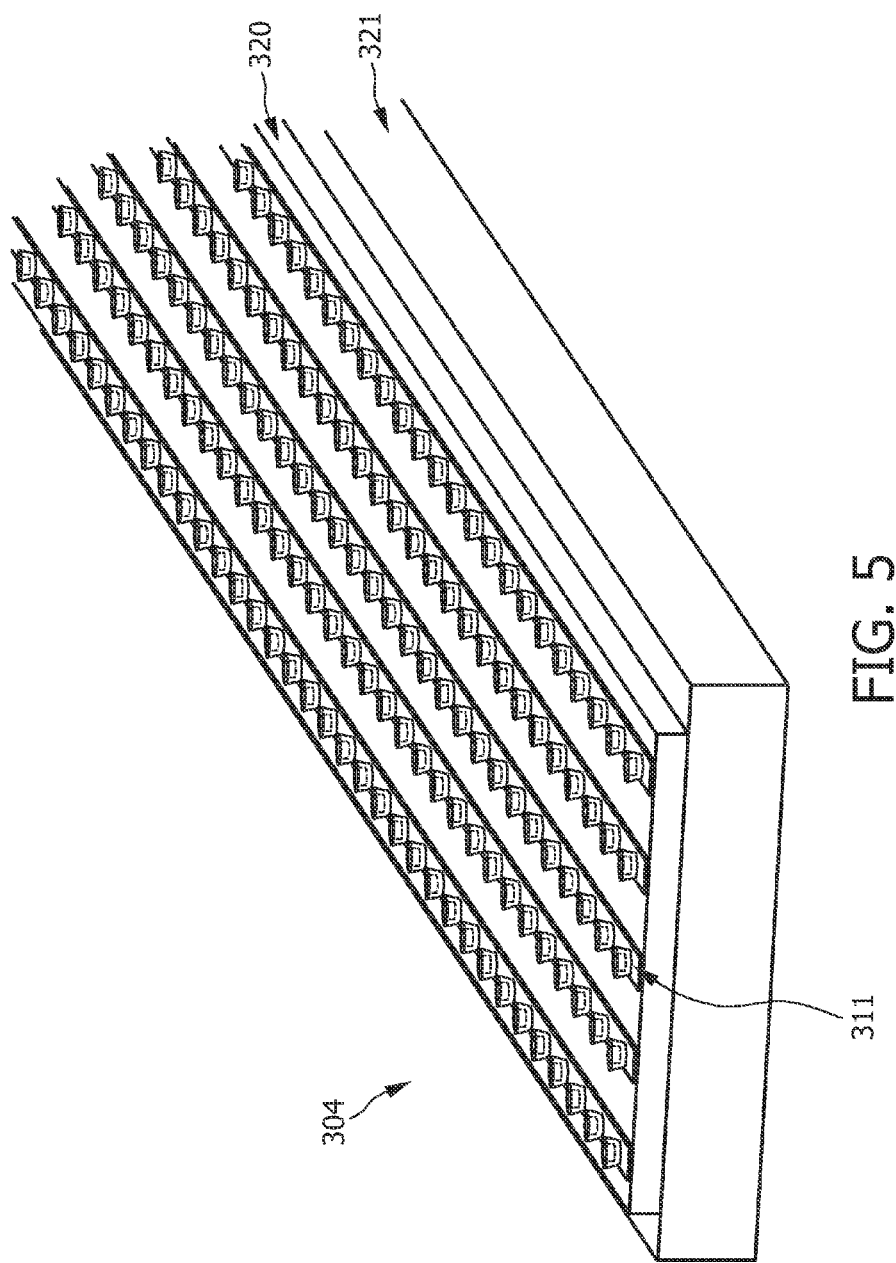
FIG. 5 shows schematically and exemplarily an arrangement of VCSELs of another embodiment of a light application apparatus and FIG. 6 shows a flowchart illustrating an embodiment of a light application method for applying light to an object.

In FIG. 3 the array 11 of VCSELs 12 is shown as comprising three lines of VCSELs 12 in the length direction 13. However, the light application apparatus can also comprise more or less lines of VCSELs. Moreover, each line can comprise more or less VCSELs. FIG. 5 shows schematically and exemplarily a light source 304, which can be used together with the further elements described above with reference to FIGS. 1 to 3 of a light application apparatus for applying light to an object. The light source 304 comprises an array of VCSELs 311 comprising five lines of VCSELs defining five different sub-groups. Also these five sub-groups can be addressed separately from each other by the control unit 9. In particular, the different sub-groups can emit the same and/or different wavelengths, and/or the same and/or different intensities to provide a desired illumination profile.

Layer 320 is the submount on which the VCSELs are mounted. Such submounts are, for example, made from aluminium oxide, aluminium nitride, ceramic, or beryllium oxide, plated with, for example, copper, gold, silver, palladium silver or other metals or metal compounds. Alternatively, the VCSELs can be mounted directly on a copper submount. Layer 321 serves as a heat spreader and heat sink and is, for example, made from aluminum or copper.

Referring again to FIGS. 1 to 3, the control unit 9 is adapted to control the light source 4 such that the processing light 2 is generated depending on the detected sensing light 5, in particular, the control unit is adapted to control the light source such that the processing light is generated depending on an amplitude of a signal generated by the light detector indicative of the detected sensing light. The detected sensing light 5 is indicative of a property of the object 3. Thus, by controlling the light source 4 such that the processing light 2 is generated depending on the detected sensing light 5, the processing of the object 3 can be performed in accordance with the property of the object 3.

In this embodiment, the control unit 9 is adapted to determine a property of the object 3 from the detected sensing light 5 and to control the light source 4 such that the processing light 2 is generated depending on the determined property of the object 3. Thus, the application of the processing light 2 can be performed depending on the detected sensing light 5 directly, or the application of the processing light 2 can be performed depending on a property of the object, which is determined from the detected sensing light 5.

It is further preferred that the control unit 9 is adapted to determine an absorption of the sensing light 5 from the detected sensing light 6 and to control the light source 4 such that the processing light 2 is generated depending on the determined absorption. This allows controlling the processing light 2 depending on the absorption properties of the object 3.

The control unit 9 can further be adapted to determine another property of the object 3, in particular, based on the absorption of the sensing light 5. For example, the skin type and/or skin tone and/or the degree of tanning can be determined based on the detected sensing light 5, in particular, based on the determined absorption. The control unit 9 preferentially comprises a look-up table or a function defining an assignment between the determined property of the object 3, in particular, the determined absorption of the sensing light 5, and properties of the processing light 2. Thus, after the property of the object 3 has been determined, the processing light 2 can be generated in accordance with the properties of the processing light 2 stored in the control unit 9. The corresponding assignments between the determined properties of the object 3 and the properties of the processing light 2 are determined by calibration measurements. For determining a property of the object 3 depending on the detected sensing light 5 also a look-up table or a function representing assignments between the detected sensing light 5 and properties of the object 3 can be used, wherein these assignments can also be determined by calibration measurements. For example, the sensing light 5 can be applied to an object 3 having a known property, wherein the detected sensing light 5 is assigned to the known property of the object 3 for generating a corresponding assignment. The absorption of the sensing light is preferentially determined in accordance with following equation:

$$I_0 = I_S \cdot e^{-x_g \alpha_g}, \qquad (2)$$

wherein $x_g$ indicates the distance between the light source and the light detector and wherein $\alpha_g$ indicates an absorption coefficient of the object, which can be regarded as an effective absorption coefficient. The distance $x_g$ is known such that by measuring the intensities $I_0$ emitted by the light source and $I_S$ detected by the light detector the absorption coefficient $\alpha_g$ can be determined. The control unit 9 can adapted to control the generation of the processing light 2 depending on the determined absorption coefficient $\alpha_g$. If the light source comprises an array of light emitting elements arranged at different locations the average location of these light emitting elements is used for determining the distance between the light source and the light detector, and if the light detector comprises several light sensing elements arranged at different locations, the average location of these light sensing elements is used for determining the distance between the light source and the light detector.

The control unit 9 can be adapted to control the light source 4 such that at the sensing time interval first sensing light is emitted from a first sub-group and then second sensing light is emitted from a second sub-group, wherein the first sensing light and the second sensing light are detected by the light detector 8 and wherein the control unit 9 is adapted to control the light source 4 depending on the detected first sensing signal and the detected second sensing signal. In particular, the control unit 9 is adapted to control the light source 4 such that the processing light 2 is generated depending on the first sensing light and the second sensing light.

The control unit 9 is preferentially adapted to control the light source 4 such that the processing light 2 is generated depending on the first sensing light and the second sensing light. It is further preferred that the control unit 9 is adapted to control the light source 4 depending on the amplitudes of a signal generated by the light detector 8, i.e. the control unit 9 is adapted to control the light source 4 depending on a first amplitude of a first signal indicative of the detected first sensing light and on a second amplitude of a second sensing signal indicative of the detected second sensing light.

These amplitudes are indicative of the optical properties of the object 3 and thus of the penetration depth of the processing light 2 into the object 3, in particular, into the skin. Thus, by adapting the control unit 9 such that the processing light 2 is generated depending on the detected first sensing light and the detected second sensing light, the processing light 2, in particular, the intensity and the wavelength, can be adapted to the respective penetration depth of the processing light 2 into the object 3.

It is further preferred that the object 3 is the skin of a human being or of an animal, wherein the control unit 9 is adapted to determine an absorption of the first and second sensing light in the epidermis of the skin and an absorption of the first and second sensing light in the dermis from the detected first sensing light and the detected second sensing light to control the light source 4 such that the processing light 2 is generated depending on at least one of the determined absorption in the epidermis and the determined absorption in the dermis, in particular, depending on at least one of a determined absorption coefficient of the epidermis and a determined absorption coefficient of the dermis. In particular, the control unit 9 is adapted to control the light source 4 such that the processing light 2 is generated depending on the determined absorption in the epidermis.

On its way from the light source 4 to the light detector 8 the sensing light passes a first time through the epidermis, then through the dermis, and finally a second time through the epidermis. The epidermis is the topmost layer of the skin and generally only about 0.1 mm thick. The epidermis contains melanin that absorbs light and determines skin tone and degree of tanning. Light scattering in the epidermis is relatively weak and can generally be neglected due to the small thickness of this layer of the skin. Underneath the epidermis is the dermis which has generally a thickness of several millimeters. In the dermis light is absorbed by hemoglobin and water. Furthermore, light is also scattered in the dermis which makes it spread parallel to the surface of the skin and reach the light detector 8. Light spreading from the light source 4 to the light detector 8 can roughly be characterized by an exponential attenuation of its intensity from the light source 4 to the light detector 8 according to equation (1).

If the distance traveled by the first sensing light in the dermis is different from the distance traveled by the second sensing light in the dermis, then the first amplitude of a first signal indicative of the detected first sensing light and the second amplitude of a second signal indicative of the detected second sensing light allow for determining the absorption coefficient $\alpha_e$ of the epidermis and the absorption coefficient $\alpha_d$ of the dermis, wherein it is assumed that the distance $x_e$ traveled by the sensing light in the epidermis is twice the thickness of the epidermis which is known and about 0.1 mm and that the distance $x_d$ traveled by the sensing light in the dermis is given by the distance between the light source 4 and the light detector 8. If the light source 4 comprises an array 11 of light emitting elements arranged at different locations, the distance $x_d$ is preferentially assumed as being the distance between an average location of the light emitting elements and the location of the light detector 8. If the light detector 8 comprises several light sensing elements arranged at different locations, an average location of these light sensing elements is preferentially used for determining the distance between the light source 4 and the light detector 8. Then skin tone/type and degree of tanning can be determined from the absorption properties of the epidermis, i.e. from $\alpha_e$.

The absorption coefficients $\alpha_e$ and $\alpha_d$ can be regarded as effective absorption coefficients.

In order to control the light source 4 such that the processing light 2 is generated depending on the absorption of the sensing light, the control unit 9 comprises preferentially a look-up table or a function assigning properties of the processing light 2 to the determined absorption of the sensing light. For example, the intensity and/or the wavelength of the processing light 2 can be assigned to absorption coefficients determined by the control unit 9. The assignments between the properties of the processing light 2 and the absorption of the sensing light can be determined in advance by calibration measurements. For example, if for a skin of a human being or of an animal optimized properties of processing light 2 are known, the absorption of the sensing light can be determined for the skin and the determined absorption can be assigned to the optimized properties of the processing light 2 for generating an assignment, which can be stored in the control unit 9.

In an embodiment, the array of VCSELs comprises a spatial density of the VCSELs being larger at an end of the array than within the array. If the array of VCSELs is a two-dimensional array, the end can be regarded as the edge of the array, i.e. in this case the spatial density of the VCSELs is preferentially larger at an edge of the array than within the array.

A location of the object 3, to which the processing light 2 is directed, is not influenced by a single VCSEL 12, but by several neighbored VCSELs. Since at the end of the array of VCSELs the VCSELs have a reduced number of neighbors, the intensity of the processing light 2 being used for processing the object 3 is reduced at the end of the array of VCSELs, because less VCSELs influence the respective location of the object 3. If at the end of the array of the VCSELs the spatial density of the VCSELs is larger than within the array, this larger spatial density can counteract the reduced processing effect at the end of the array of the VCSELs. In particular, the spatial density of the VCSELs at the end of the array of VCSELs is adapted such that a location of the object 3 arranged at the end of the array of VCSELs receive the same intensity as a location of the object 3 arranged more centrally with respect to the array of VCSELs.

Figure 6:
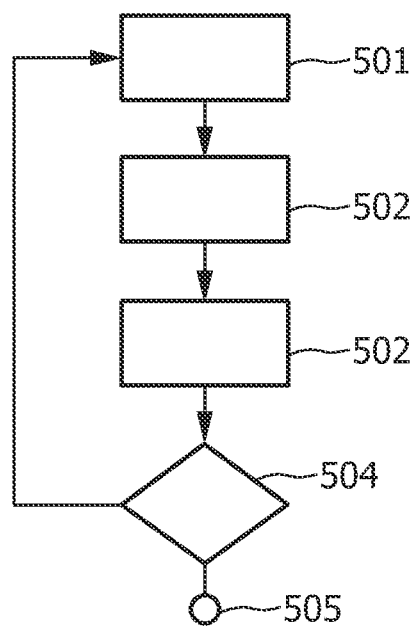

An embodiment of a light application method for applying light to an object will in the following be described with reference to a flowchart shown in FIG. 6.

In step 501, the control unit 9 controls the light source 4 such that the light source 4 generates sensing light 5 in a sensing time interval. The sensing light is coupled into the object 3.

In step 502, the sensing light 5 is detected by the light detector 8, after the sensing light has traveled through the object 3 and has left the object 3.

In step 503, the control unit 9 controls the light source 4 such that the light source 4 generates processing light 2 in a processing time interval depending on the detected sensing light. The processing light is coupled into the object 3 for treating the object, in particular, for removing hair from skin.

In step 504, it is decided whether the application of light should stop or should continue. For example, a user can stop the application of light by switching off the light application apparatus. In this case, the light application method ends in step 505. If the light application method should continue, for example, because the light application apparatus is not switched off, the light application method continues with step 501.

The sensing time interval is preferentially smaller than the processing time interval. In particular, the sensing time interval has preferentially a duration of some 100 microseconds, for example, less than 10 milliseconds, further preferred less than one millisecond, whereas the processing time interval has a duration of at least some milliseconds, for example, a duration being larger than 10 milliseconds, further preferred larger than 100 milliseconds, and even further preferred larger than one second.

The light application apparatus is preferentially used for photothermal epilation and skin treatment applications, wherein an array of VCSELs offers multiple benefits like an ideal wavelength range, a planar source, power saving and reliability. In addition, the array of VCSELs offers the opportunity to integrate optical sensors, which allow a feedback from the skin.

A single photodiode can be used in combination with a laser array and a special electrical addressing for sensing the skin. The light application apparatus and the light application method allow an online measurement of absorption of infrared radiation in the skin, which give a reliable feedback on the skin type and the degree of tanning. This allows a fully self-adaptive system. Thus, the property determination unit is preferentially adapted to determine the skin type and/or the degree of tanning depending on the detected sensing light, wherein the control unit is adapted to control the generation of the processing light depending on the determined skin type and/or the determined degree of tanning.

The sensing light can emit light having different wavelengths. This allows measuring a wavelength dependent penetration of radiation into the skin. This wavelength dependent penetration of radiation can be used to generate the processing light such that individual wavelengths of the processing light are dimmed to a level optimizing the desired penetration profile.

Instead of using VCSELs other kind of light emitting elements can be used like flash-lamps and lasers. In an embodiment, the processing light has a wavelength in the range of 570-1200 nm, an energy density in the range of 2-30 J/cm$^2$ and a pulse duration within 1-600 ms.

The light application apparatus is preferentially adapted to heat the hair follicle above a certain temperature while minimizing unwanted side effects like skin burning and pain. The ideal wavelength and the optimum dose of the processing light depend on individual parameters like skin type, degree of tanning et cetera and require therefore individual settings. These settings are determined depending on the detected sensing light by the control unit 9.

For applying light to the object the light source comprises preferentially lasers like an array for VCSELs, because lasers offer a narrow spectral emission, allow to control the power density accurately and to tailor the maximum absorption in the melanin of the hair follicle with respect to the absorption in the surrounding skin, in order to perform an efficient epilation with less pain and side effects.

The array of VCSELs represents a cost effective way to provide the required laser power, which amounts preferentially to a few 10 W, and offers several additional advantages. The planar arrangement of many VCSELs allows adapting the form factor. A single VCSEL has preferentially a power of about 100 mW. The array of VCSELs comprises therefore preferentially some hundreds of VCSELs. For an epilation procedure with a continuously moving handheld apparatus like the apparatus shown in FIG. 4, it can be advantageous to arrange the VCSELs along a line, in particular, along multiple lines. Furthermore, such a planar arrangement of many VCSELs simplifies heat sinking.

The emission characteristics of VCSELs within a slightly diverging cone allow using them without additional optics like lenses or reflectors simply in a distance of few millimeters to the skin. This leads to costs efficient and flat system. Moreover, VCSELs can be produced in the wavelength range of 600-1100 nm with high power conversion efficiency and at low cost.

The array of VCSELs, which is preferentially a planar arrangement of VCSELs, comprises preferentially one long axis being the length direction and one short axis being the width direction. For a continuous treatment of the skin the handheld apparatus is preferentially moved along the short axis.

The VCSELs are preferentially electrically connected in individual sub-groups to the control unit, which can also be regarded as an electronic driver. The sub-groups consist, for example, of VCSELs with the same wavelengths and/or VCSELs around a certain geometrical location, for example, towards one side of the array or the opposite side.

The light detector is preferentially an electro-optical sensor like a photodiode, which is arranged at a position, that the average distance to the VCSELs in individual sub-groups is different. The sensing light of one sub-group penetrates the skin, is scattered in all directions and travels therefore through the skin, for example, towards the light detector, escapes the skin and hits the light detector. Sensing light from different sub-groups has to travel a different distance in the skin towards the light detector. The signal strength contains therefore information about the optical properties of the skin, especially about absorption and scattering.

The light detector receives sensing light, preferentially only from a well defined skin area next to it. This ensures that the sensing light, which is detected by the light detector, is really traveling through the skin. This is realized by the aperture 10 around the light detector 8, which has preferentially the shape of a funnel and is preferentially in contact with the skin at least during the sensing time interval.

Preferentially, during the sensing time interval only one sub-group is operated at a time. This allows to know from which sub-group the sensing light received by the light detector is emitted. The resulting signals generated by the light detector can be recorded in correlation to the respective sub-group, which was operated at the time of measurement. The results are stored in the control unit and the treatment parameters are chosen in relation to these measurements, i.e. the control preferentially comprises a look-up table, in which settings of the processing light are stored depending on the detected sensing light. This means, assignments are stored between the detected sensing light and the settings of the processing light, which should be used for processing the object, if the light detector detects the respective sensing light. These assignments can be determined by, for example, calibration measurements such that the processing of the object is optimized depending on the sensing light detected by the light detector.

The array 11 of VCSELs 12 shown in FIG. 3 comprises six sub-groups 111, 112, 113, 121, 122, 123. However, the control unit 9 can also be adapted such that some of these sub-groups are controlled similarly such that these some sub-groups, which are controlled similarly, could be regarded as a single sub-group. For example, the three sub-groups 111, 112, 113 could be controlled similarly and the three sub-groups 121, 122, 123 could also be controlled similarly such that the array 11 shown in FIG. 3 can be regarded as being comprised of two sub-groups, a first sub-group consisting of the sub-groups 111, 112, 113 and a second sub-group consisting of the sub-groups 121, 122, 123. For example, the first sub-group can be controlled such that during a first time interval within the sensing time interval only the first sub-group emits sensing light, which travels through the skin and is finally detected by the light detector, and that during a second time interval within the same sensing time interval the second sub-group emits sensing light to the object, which travels through the object and is finally detected by the light detector. Thus, in this way first sensing light is detected during the first time interval and second sensing light is detected during the second time interval.

Since different sub-groups are preferentially connected to the control unit 9 such that different sub-groups can be addressed differently, different sub-groups can emit sensing light and/or processing light having different wavelengths. Preferentially, the power level, i.e. the intensity, of the processing light and/or the sensing light is chosen depending on the absorption property of the respective wavelength, which depends on the absorption property of the respective skin type. However, VCSELs of different sub-groups could also be set to different power levels, even if operating at the same wavelength in order to obtain a certain desired irradiation profile. For example, the sub-groups 121, 123 could be set to a different power level than the sub-group 122, even if operating at the same wavelength. This is especially advantageous, because the heat dissipation to the sides is stronger than for the center of the array of VCSELs.

If the direction of movement is known, for example, from a velocity measurement performed by the velocity measurement unit 15, the three lines shown in FIG. 3 can be operated at different power levels to obtain a favorable temperature ramp over time while the light source 4 is moved across a point of the skin.

The detected sensing light, in particular, a property of the object determined depending on the detected sensing light, can be used to determine at least one of the following settings of the processing light: intensity; wavelength; repetition frequency, if the processing light is repeatedly and interruptedly applied to the object; pulse duration if processing light is applied in a pulsed way, et cetera.

Although in the above described embodiments the light source preferentially comprises VCSELs, in other embodiments the light source can comprise other light emitting elements. For example, the light source can comprise a solid-state light source like light emitting diodes, organic diodes and/or laser diodes. A preferred laser diode is the VCSEL. However, also an edge-emitting laser diode can be used as light emitting element of the light source.

Although the above described light application apparatus and light application method are preferentially adapted to remove hair from the skin of a person, the light application apparatus can also be used for performing another kind of processing on another kind of object, for example, a treating of a surface of a technical object.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of settings of the processing light depending on detected sensing light directly or depending on a determined property of the object or like a determination of a property of the object performed by one or several units or devices can be performed by any other number of units or devices. The determinations and/or the control of the light application apparatus in accordance with the light application method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A light application apparatus for applying light to an object, the light application apparatus comprising:
   a light source for generating processing light for processing the object and sensing light for sensing the object, the light source being adapted to couple the processing light and the sensing light into the object,
   a light detector for detecting the sensing light after having left the object, and
   a control unit for controlling the light source such that the light source alternately generates processing light in a processing time interval and sensing light in a sensing time interval;
   wherein the light source comprises an array of light emitting elements separated into sub-groups, wherein the control unit is adapted to control the light source such that at the sensing time interval first sensing light is emitted from a first sub-group and then second sensing light is emitted from a second sub-group, wherein the first sensing light and the second sensing light are detected by the light detector, wherein the control unit is adapted to control the light source depending on the detected first sensing light and the detected second sensing light; and,
   wherein the object is the skin of a human being or of an animal, wherein the control unit is further adapted to determine an absorption of the first and second sensing light in the epidermis of the skin and an absorption of the first and second sensing light in the dermis of the skin from the detected first sensing light and the detected second sensing light and to control the light source such that the processing light is generated depending on at least one of the determined absorption in the epidermis and the determined absorption in the dermis.

2. The light application apparatus as defined in claim 1, wherein the light source comprises a vertical-cavity surface-emitting laser.

3. The light application apparatus as defined in claim 1, wherein the array of light emitting elements of at least one sub-group are arranged such that the spatial density of the sub-group's light emitting elements is larger at an end of the array than within the array.

4. The light application apparatus as defined in claim 1, wherein the array of light emitting elements of at least one sub-group are arranged in a rectangular shape having a length dimension in a length direction and a width dimension in a width direction, wherein the length dimension is larger than the width dimension.

5. The light application apparatus as defined in claim 4, wherein the light detector is arranged beside the array of the light emitting elements in the length direction.

6. The light application apparatus as defined in claim 1, wherein the control unit is adapted to control the light source such that only one sub-group emits sensing light at a time in the sensing time interval.

7. The light application apparatus as defined in claim 1, wherein the light application apparatus further comprises an aperture around the light detector for ensuring that light is detected which mainly comes from the object.

8. The light application apparatus as defined in claim 1, wherein the control unit is adapted to determine an absorption of the sensing light from the detected sensing light and to control the light source such that the processing light is generated depending on the determined absorption.

9. The light application apparatus as defined in claim 1, wherein the light application apparatus is an epilation apparatus.

10. A light application method for applying light to the skin of a human being or of an animal, the light application method comprising following steps:
   generating processing light for processing the object and sensing light for sensing the object by a light source and coupling the processing light and the sensing light into the object,
   detecting the sensing light after having left the object by a light detector, and
   controlling the light source such that the light source alternately generates processing light in a processing time interval and sensing light in a sensing time interval by a control unit;
   arranging the light source into an array of light emitting elements separated into sub-groups, wherein the control unit is adapted to control the light source such that at the sensing time interval first sensing light is emitted from a first sub-group and then second sensing light is emitted from a second sub-group, wherein the first sensing light and the second sensing light are detected by the light detector, wherein the control unit is adapted to control the light source depending on the detected first sensing light and the detected second sensing light; and, wherein the control unit is further adapted to determine an absorption of the first and second sensing light in the epidermis of the skin and an absorption of the first and second sensing light in the dermis of the skin from the detected first sensing light and the detected second sensing light and to control the light source such that the processing light is generated depending on at least one of the determined absorption in the epidermis and the determined absorption in the dermis.

* * * * *